United States Patent [19]
Pray et al.

[11] Patent Number: 5,533,987
[45] Date of Patent: Jul. 9, 1996

[54] DILATATION CATHETER WITH POLYMIDE ENCASED STAINLESS STEEL BRAID PROXIMAL SHAFT

[75] Inventors: James R. Pray, New Hope; Richard G. Cornelius, Golden Valley, both of Minn.; Michelle Arney, Menlo Park, Calif.

[73] Assignee: Scimed Lifesystems, Inc., Maple Grove, Minn.

[21] Appl. No.: 563,888

[22] Filed: Nov. 22, 1995

Related U.S. Application Data

[63] Continuation of Ser. No. 108,679, filed as PCT/US93/03352, Apr. 9, 1993, abandoned, which is a continuation-in-part of Ser. No. 867,164, Apr. 9, 1992, Pat. No. 5,338,295.

[51] Int. Cl.$^6$ ...................................................... A61M 25/00
[52] U.S. Cl. ............................ 604/280; 604/282; 604/264
[58] Field of Search ..................................... 604/280, 282, 604/96–103, 264; 606/192–196; 600/18

[56] References Cited

U.S. PATENT DOCUMENTS

| | | |
|---|---|---|
| 3,485,234 | 12/1969 | Stevens . |
| 3,924,632 | 12/1975 | Cook . |
| 4,323,071 | 4/1982 | Simpson et al. . |
| 4,425,919 | 1/1984 | Alston, Jr. et al. . |
| 4,526,972 | 5/1985 | Samson . |
| 4,706,670 | 11/1987 | Andersen et al. . |
| 4,739,768 | 4/1988 | Engelson . |
| 4,776,844 | 10/1988 | Ueda . |
| 4,793,350 | 12/1988 | Mar et al. . |
| 4,811,737 | 3/1989 | Rydell . |
| 4,820,349 | 4/1989 | Saab . |
| 4,838,268 | 6/1989 | Keith et al. . |
| 4,842,590 | 6/1989 | Tanabe et al. . |
| 4,884,573 | 12/1989 | Wijay et al. . |
| 4,899,787 | 2/1990 | Ouchi et al. . |
| 4,900,314 | 2/1990 | Quackenbush . |
| 4,906,241 | 3/1990 | Noddin et al. . |
| 4,917,666 | 4/1990 | Solar et al. . |
| 4,921,483 | 5/1990 | Wijay et al. . |
| 4,955,862 | 4/1990 | Sepekta . |
| 4,964,853 | 10/1990 | Sugiyama et al. . |
| 4,976,690 | 12/1990 | Solar et al. . |
| 4,976,720 | 12/1990 | Machold et al. . |
| 4,981,478 | 1/1991 | Evard et al. . |
| 4,998,917 | 3/1991 | Gaiser et al. . |
| 5,019,057 | 5/1991 | Truckai . |
| 5,032,113 | 7/1991 | Burns . |
| 5,035,705 | 7/1991 | Burns . |
| 5,037,404 | 8/1991 | Gold et al. . |
| 5,047,026 | 9/1991 | Rydell . |
| 5,074,045 | 9/1991 | Arney et al. . |
| 5,100,381 | 3/1992 | Burns . |
| 5,105,818 | 4/1992 | Christian et al. . |
| 5,125,909 | 6/1992 | Heimberger . |
| 5,141,518 | 8/1992 | Hess et al. . |
| 5,217,440 | 6/1993 | Frassica . |

FOREIGN PATENT DOCUMENTS

| | | |
|---|---|---|
| 0249338 | 12/1987 | European Pat. Off. . |
| 0349640 | 1/1990 | European Pat. Off. . |
| 0358117 | 3/1990 | European Pat. Off. . |
| 0368523 | 5/1990 | European Pat. Off. . |
| 0420486 | 4/1991 | European Pat. Off. . |
| 0428976 | 5/1991 | European Pat. Off. . |
| 0444728 | 9/1991 | European Pat. Off. . |
| WO87/00442 | 1/1987 | WIPO . |
| WO89/08471 | 9/1989 | WIPO . |
| WO90/01406 | 2/1990 | WIPO . |
| WO93/23107 | 11/1993 | WIPO . |

*Primary Examiner*—John D. Yasko
*Attorney, Agent, or Firm*—Vidas, Arrett & Steinkraus

[57] ABSTRACT

The present invention provides a catheter for insertion into the body and having proximal and distal ends, the distal end preceding and the proximal end trailing when said catheter is inserted into the body, said catheter comprising an inner tubular shaft and an outer tubular shaft having a proximal outer tube section and a distal outer tube section, the proximal outer tube section further having proximal and distal ends, the proximal outer tube section comprising a polymer encased tubular braid of stainless steel, the polymer encasement for the braid comprising at least one layer of polyimide, the braid having a weave which increases in pick count from the proximal end to the distal end of the proximal outer tube section.

6 Claims, 4 Drawing Sheets

DILATATION CATHETER WITH POLYMIDE ENCASED STAINLESS STEEL BRAID PROXIMAL SHAFT

This is a continuation of application No. 08/108,679, filed as PCT/US93/03352, Apr. 9, 1993, now abandoned, which is a continuation in part of Ser. No. 07/867,164 filed Apr. 9, 1992, now U.S. Pat. No. 5,338,295.

BACKGROUND OF THE INVENTION

The present invention relates to a dilatation catheter for use in angioplasty. Angioplasty has gained wide acceptance as an efficient and effective method of opening stenoses in the vascular system. In the most widely used form of angioplasty, a dilatation balloon catheter is guided through the vascular system until a balloon, which is mounted at the distal end of the catheter shaft, is positioned across the stenosis. The balloon is then inflated to open the artery and reestablish acceptable blood flow.

Dilatation catheters can generally be divided into those which are fed over a guide wire (i.e., "over the-wire" catheters) and those catheters which serve as their own guide wire (i.e., "fixed-wire" catheters). Both types of catheters have advantages and disadvantages.

Innerless dilatation balloon catheters have been developed in an attempt to obtain some of the advantages of a fixed-wire catheter while still retaining the advantages of an over-the-wire catheter. These innerless catheters feature a shaft having a single lumen which acts as both an inflation lumen and a guide wire lumen. A lumen extension extends through the balloon, which is mounted on the distal end of the shaft. The shaft lumen is in fluid communication with the interior of the balloon. The guide wire extends through the shaft lumen, the lumen extension and out the distal end of the balloon.

Examples of innerless dilatation balloon catheters are shown in U.S. Pat. Nos. 5,032,113 and 5,035,705 by Matthew M. Burns.

When used in percutaneous transluminal coronary angioplasty (PTCA), the dilatation catheter is typically advanced through a guide catheter to the aorta. Using fluoroscopy, the physician manipulates the catheter until the balloon is located across the stenosis. This may involve the use of a guide wire over which the catheter is moved. Alternatively, the catheter may act as its own guide wire, depending upon the particular design. The manipulation of the dilatation catheter through the guide catheter and through the coronary arteries to the stenosis requires the dilatation catheter to have a number of different, sometimes conflicting, characteristics.

For example, a successful dilatation catheter must offer flexibility so that the catheter can maneuver through tight curvatures of the vascular system. A dilatation catheter also must allow the physician to transmit longitudinal force along the dilation catheter from its proximal end to its distal end so the catheter can be pushed through the guide catheter and arteries and across the stenosis. This characteristic is referred to as pushability. Typically, the outer dimensions of all parts of the dilatation catheter, including particularly the shaft, should be minimized. Friction between the dilatation catheter, the guide catheter and the guide wire, respectively, should also be minimized.

Prior dilatation catheters typically reflected trade-offs between these and other characteristics. For example, catheters having shafts with sections of different materials have been used in order to provide greater flexibility at the distal end of the catheter. Thin wall materials such as stainless steel hypo tubing and polyimide tubing have been used for proximal sections of dilatation catheter shafts in order to reduce the outer diameter and wall thickness of the catheter shaft.

SUMMARY OF THE INVENTION

The present invention is an improved dilatation catheter having a shaft with a proximal section formed by a composite polymer/stainless steel braid tube, and a distal section formed by a flexible polymer tube. The distal section, which is preferably a polyethylene tube, has greater flexibility than the proximal section. In one embodiment, the shaft of the present invention forms the outer tube of an over-the wire balloon catheter. In an alternative embodiment, the shaft of the present invention functions as a single-lumen shaft for either a fixed-wire balloon catheter or an innerless catheter.

In preferred embodiments of the present invention, the composite tube which forms the proximal section of the shaft has a wall thickness at its thickest points of about 0.079 mm (0.0031 inches) to about 0.089 mm (0.0035 inches). The stainless steel braid is formed by multiple strands of stainless steel member, such as a ribbon or a wire, which are woven in a "clothing weave" and are encased in a polymer matrix comprising polyimide. The stainless steel ribbon preferably has a thickness of about 0.018 mm (0.0007 inches) to about 0.025 mm (0.0010 inches) and width of about 0.071 mm (0.0028 inches) to about 0.135 mm (0.0053 inches) and the stainless steel wire preferably has a diameter in the range of 0.025 mm (0.001 inches) to 0.038 mm (0.0015 inches).

In a further embodiment, the braid weave of the proximal section of the shaft has a varying pick count, increasing in the distal direction, thereby providing an increasing flexibility as one moves in the distal direction. This feature allows for increased pushability at the proximal end of the shaft while reducing the difference in flexibility between the proximal and digital portions of the shaft at their junction.

DETAILED DESCRIPTION OF THE PREFERRED EMBODIMENTS

Figure 1:
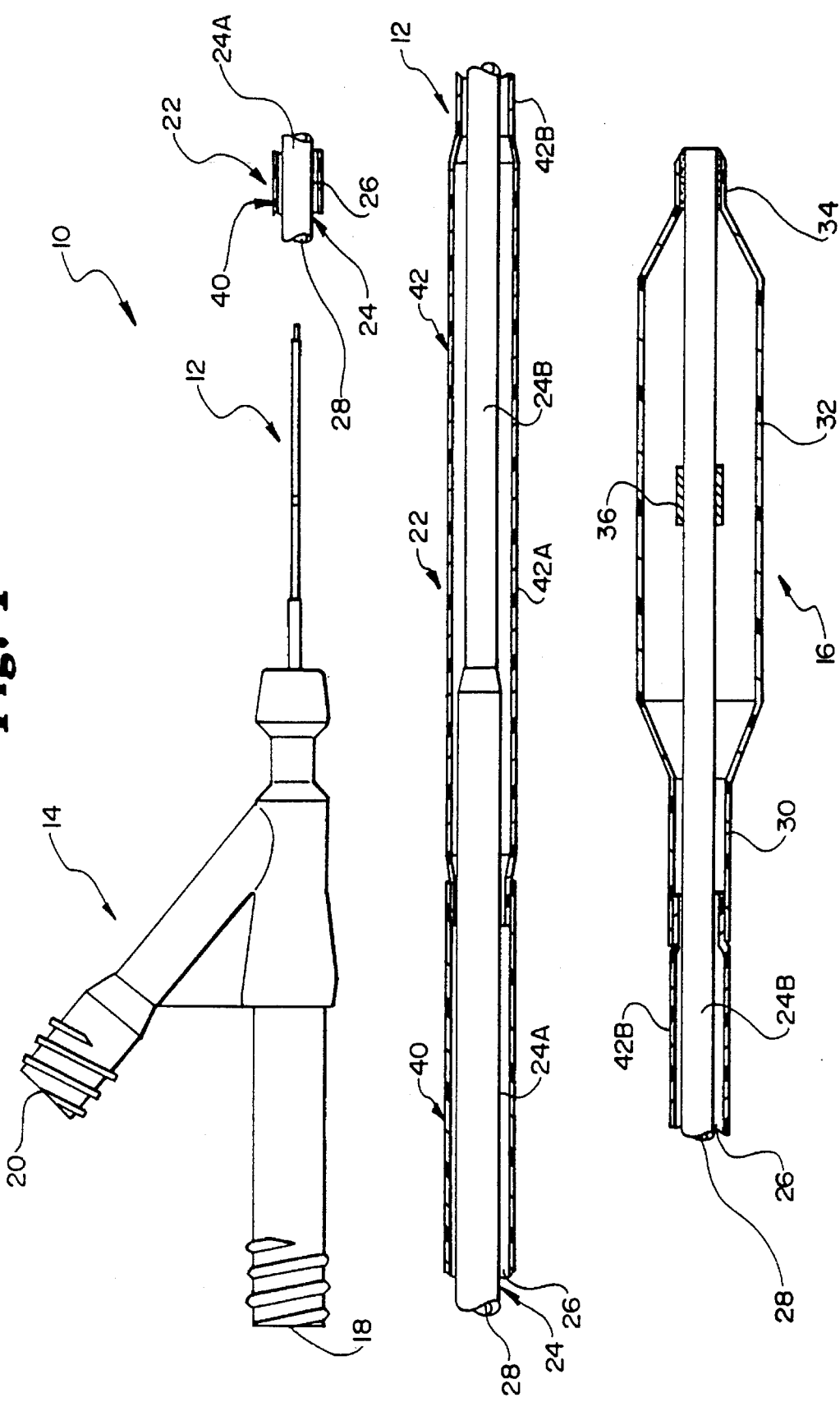
FIG. 1 is a partial sectional view of a first embodiment of the dilatation catheter of the present invention, with the distal portion of the catheter shown in a larger scale than the proximal portions.

Dilatation catheter 10 shown in FIG. 1 is an over-the-wire balloon catheter which includes shaft 12, manifold 14, and inflatable balloon 16. Manifold 14, which includes thru port 18 and balloon inflation port 20, is connected to the proximal end of shaft 12. Balloon 16 is mounted at the distal end of shaft 12.

Shaft 12 includes outer tube 22 and inner tube 24. Inflation lumen 26, which permits fluid communication between inflation port 20 of manifold 14 and the interior of balloon 16, is defined between the inner wall of outer tube 22 and the outer wall of inner tube 24.

Guide wire lumen 28 extends through the center of inner tube 24. Guide wire lumen 28 provides a path for a guide wire (not shown) from thru port 18 to the distal end of dilatation catheter 10.

Inflatable balloon 16 includes proximal balloon waist 30, intermediate inflatable portion 32, and distal end portion 34. Balloon waist 30 is connected to the distal end of outer tube 22, and distal end portion 34 of balloon 16 is connected to the distal end of inner tube 24.

Located within balloon 16 on inner tube 24 is marker band 36. In a preferred embodiment, marker band 36 is a radiopaque material, such as a platinum alloy.

Inner tube 24 is a unitary polyethylene tube having proximal section 24A and distal section 24B. Inner tube 24 is form eel by necking down the polyethylene tube so that distal section 24B has a smaller outer diameter than proximal section 24A.

Outer tube 22 is formed by two different tube materials. Proximal section 40 of outer tube 22 is a composite tube formed by a stainless steel braid which is encased in a polymer matrix comprising polyimide. In one preferred embodiment, proximal section 40 has a length of about 106.7–109.2 cm (42 to 43 inches), an outer diameter of between about 0.932 mm (0.0367 inches) and about 0.958 mm (0.0377 inches), and a wall thickness of about 0.079 mm (0.0031 inches).

In one embodiment, distal section 42 of outer tube 22 is a polymer tube, such as high density polyethylene tube, which has its proximal end bonded to the distal end of proximal section 40 and has its distal end connected to balloon waist 30. Distal section 42 of outer tube 22 has a first segment 42A and a second, smaller-diameter section 42B. In a preferred embodiment, the overall length of distal section 42 is between about 29.2–31.8 cm (11.5 and 12.5 inches), with first segment 42A having a length of about 10.2 cm (4 inches) and second segment 42B having a length of about 20.3 cm (8 inches).

The outer diameter of section 42B varies depending upon the size of the inflated outer diameter of balloon 16. For smaller balloon sizes (i.e., inflated diameters of 1.5 and 2.0 millimeters), the outer diameter of section 42B is preferably about 0.762 mm (0.030 inches) to about 0.788 mm (0.031 inches). For larger balloon sizes (i.e., inflated diameters of 2.5 to 3.5 millimeters), the outer diameter of section 42B is about 0.826 mm (0.0325 inches) to about 0.901 mm (0.0335 inches).

Outer tube 22 is flexible along its entire length. Distal section 42 of outer tube 22, however, has greater flexibility than proximal section 40. This provides the needed flexibility to allow catheter 10 to conform to the curvatures of the patient's vascular system. The composite polyimide-encased stainless steel braid tube which forms proximal section 40 offers enhanced pushability and a relatively small wall thickness, so that the outer diameter of outer tube 22 can be kept to a minimum.

Figure 2:
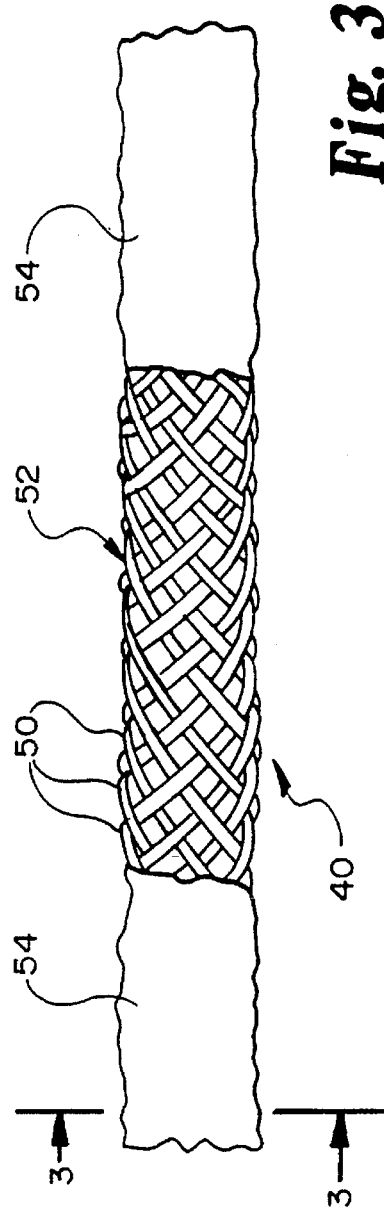
FIG. 2 is a front view, with portions broken away, showing the outer surface of the composite tube which forms the proximal shaft section of the dilatation catheter of FIG. 1.
Figure 3:
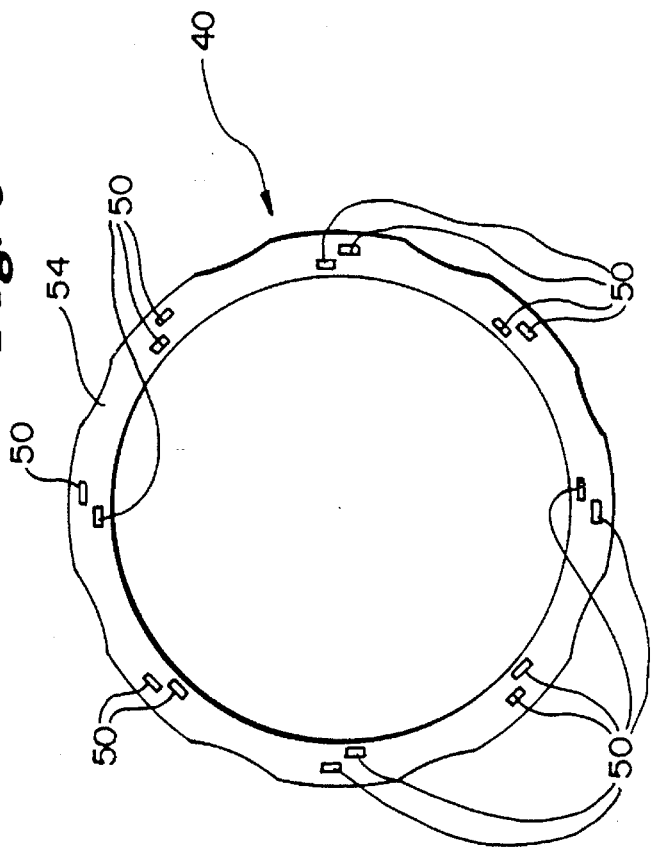
FIG. 3 is a cross-sectional view of the composite tube taken on line 3—3 of FIG. 2.

FIGS. 2 and 3 illustrate in greater detail the composite polyimide-encased stainless steel braid tube which forms proximal section 40 used in the catheter of the present invention. Individual strands of stainless steel ribbon 50 are interwoven as shown in FIG. 2 to form a tubular braid 52. Polymer matrix material 54 encases tubular braid 52. The polymer matrix material 54 suitably comprises polyimide and is thick enough to provide structural integrity to tube 40, so that proximal tube section 40 can contain fluid without leaking. Portions of individual strands of tubular braid 52 on the inner surface thereof may be exposed so long as they are effectively entrained in the polyimide matrix and the tube does not leak. The polymer matrix material 54 which encases braid 52 is thin enough so that it conforms generally to the outer surface of woven braid 52. This is illustrated in FIGS. 2 and 3, which show the relatively textured outer surface of proximal tube section 40. This exterior surface texture or roughness of proximal tube section 40 is a significant advantage. It reduces the points of contact (and drag) between proximal tube section 40 and the inner surface of the guide catheter (not shown) through which dilatation catheter 10 must be advanced. The rough surface of the composite polyimide-encased stainless steel tube of proximal section 40 of outer tube 22 exhibits significantly less drag in the guide catheter than smooth-surfaced polyimide proximal tube sections of similar dilatation catheters.

In a preferred embodiment of the present invention, individual strands 50 are 304 spring temper stainless steel ribbon having a thickness of about 0.018 mm (0.0007 inches) and a width of about 0.005 inches). Sixteen strands are woven together in a clothing weave to form tubular braid 52, with the weave being about 17.8–35.4 picks/cm (45 to 90 picks/inch). The composite wall thickness of proximal tube section 40 (i.e., braid 52 plus polyimide material 54 at the thickest points) is between about 0.064 and 0.102 mm (0.0025 and 0.0040 inches), and preferably is about 0.079 mm (0.0031 inches) to about 0.089 mm (0.0035 inches). The stainless steel braid/polyimide composite tube described is manufactured by HV Technologies of Trenton, Ga.

Thinner walled proximal sections of a catheter shaft have been made of stainless steel hypo tubing or polyimide tubing in the past. The combination of composite proximal tube section 40 and the more flexible polyethylene distal tube section 42 of the present invention, however, offers a number of significant advantages.

First, the drag coefficient of the textured exterior surface of proximal tube section 40 is significantly less than smooth-surfaced polyimide proximal tube sections of similar dilatation catheters. Therefore, the proximal tube section 40 of the present invention advances more easily through the guide catheter.

Second, the present invention offers improved pushability when compared to catheters using a thin wall polyimide tube for the proximal section.

Third, the catheter of the present invention exhibits less tendency for kinking during preparation for a dilatation procedure or during a dilatation procedure than prior art catheters which use high strength materials such as stainless steel and polyimide at the proximal section. This is because the stiffness transition between sections 40 and 42 is less abrupt than the stiffness transition between a proximal stainless steel hypo tube and a more flexible polymer distal section. In the case of polyimide proximal sections, the kinking tendency exists because the thin walls have brittle characteristics.

Finally, composite proximal tube section 40 used in catheter 10 of the present invention is more flexible than a stainless steel hypo tube proximal outer tube section. As a result, catheter 10 of the present invention is easier to handle when removing the catheter from its packaging and preparing it for use.

Figure 4:
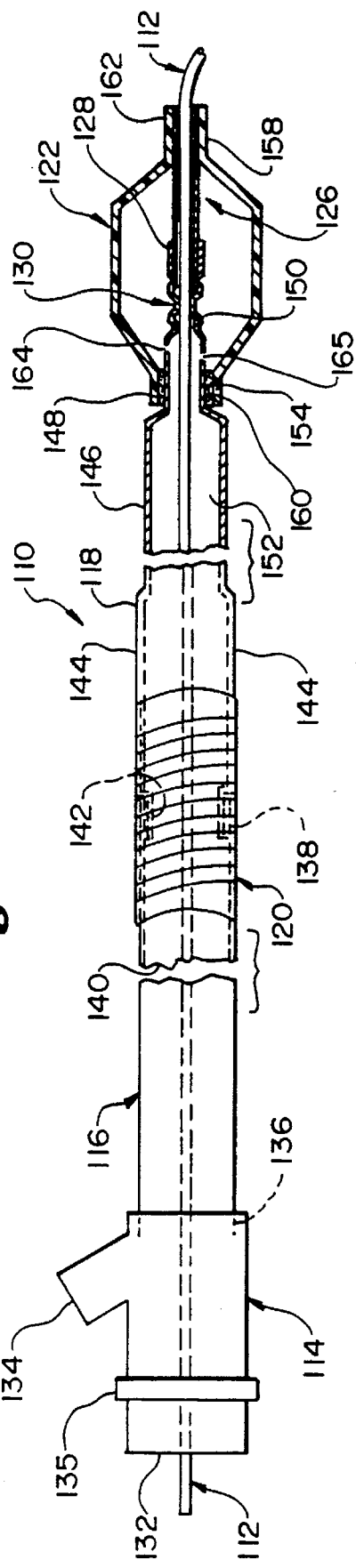
FIG. 4 is a partial sectional view of a second embodiment of the present invention as applied in a innerless dilatation catheter.

FIG. 4 is a partial sectional view of a second embodiment of the present invention functioning as an innerless dilatation catheter. FIG. 4 shows dilatation catheter 110 and guide wire 112, which are used to perform angioplasty procedures. Dilatation catheter 110 includes manifold 114, proximal shaft 116, distal shaft 118, strain relief 120, balloon 122, proximal lumen extension 124, distal lumen extension 126, marker band 128, and stretch responsive valve 130.

Manifold 114 is located at the proximal end of the dilatation catheter 110. Manifold 114 includes thru port 132 (through which guide wire 112 passes), balloon port 134 (through which inflation fluid is provided to and withdrawn from balloon 122) and manifold valve 135.

Proximal shaft 116 is a single lumen tube having its proximal end 136 connected to manifold 114, and its distal end 138 connected to distal shaft 118. Shaft lumen 140 extends from proximal end 136 to distal end 138 of shaft 116. Lumen 140 is in fluid communication with balloon port 134 and thru port 132 of manifold 114, and also provides a passage for guide wire 112.

Proximal shaft 116 is preferably a polyimide/stainless steel braid composite tube from HV Technologies of Trenton, Ga. with an inner diameter of about 0.673 mm (0.0265 inches) and an outer diameter of about 0.838 mm (0.033 inches). The length of proximal shaft 116 is about 103 centimeters.

Strain relief 120 is a 0.025 mm (0.001 inch) by 0.102 mm (0.004 inch) stainless steel ribbon which is wrapped around proximal shaft 116 and distal shaft 118 and covered by a heat-shrunk polymer sheath. Strain relief 120 has an outer diameter of about 0.965 mm (0.038 inches) and a length of about 2.5 centimeters.

Distal shaft 118 includes proximal neck section 142, shaft sections 144 and 146, bond neck section 148, and valve neck section 150. Proximal neck section 142 is bonded to distal end 138 of proximal shaft 116. In a preferred embodiment of the present invention, distal shaft 118 and distal lumen extension 126 are formed of high density polyethylene tubing and are formed as one piece by a series of necking operations. Distal lumen extension 126 is subsequently severed from valve neck section 150 to create the gap for valve 130.

Strain relief 120, which is preferably a wrapped stainless steel ribbon covered by a thin heat shrunk polymer sleeve, fits over the bond between distal portion of shaft 116 and the proximal portion of shaft 118. Strain relief 120 provides additional strength at the bond between shafts 116 and 118, particularly when tension is applied to the bond. In an alternative embodiment, the bond between shafts 116 and 118 is strong enough to avoid the need for strain relief 120.

Shaft section 144 of distal shaft 118 has an outer diameter which is equal to or slightly less than the outer diameter of proximal shaft 116. In the embodiment shown in FIG. 4, shaft section 146 is positioned intermediate to shaft section 144 and bond neck section 148. Shaft section 146 has a reduced outer and inner diameter with respect to section 144 and, in the preferred embodiment, has a greater flexibility than proximal shaft 116 and shaft section 144 of distal shaft 118.

Bond neck section 148 has a reduced outer and inner diameter with respect to shaft section 146. Valve neck section 150 has a reduced outer and inner diameter with respect to bond neck section 148. Bond neck section 148 and valve neck section 150 together form proximal lumen extension 124. Distal shaft 118 has a lumen 152 which is aligned with lumen 140 of proximal shaft 116.

Balloon 122 includes proximal balloon waist 154, main balloon body 156, and distal end section 158. Proximal balloon waist 154 is bonded to bond neck section 148 by adhesive 160. Similarly, distal end section 158 of balloon 122 is bonded by adhesive 162 to the distal end of distal lumen extension 126.

As shown in FIG. 4, guide wire 112 extends from thru port 132 of manifold 114, through shaft lumens 140 and 152, through proximal lumen extension 124 (formed by bond neck section 148 and valve neck section 150), through stretch responsive valve 130, through distal lumen extension 126 and out the distal end 158 of balloon 122 of catheter 110.

Inflation of balloon 122 is effected by passing fluid (not shown) through lumens 140 and 152 and vent holes 164 and 165 in proximal lumen extension 124. The fluid flow resistance through vent holes 164 and 165 is preferably less than the fluid resistance between guide wire 112 and the remainder of the lumen extension distal to vent holes 164 and 165. In this way, it is possible to supply inflation fluid under pressure to the interior of balloon 122 through the same lumen 140, 152 used by guide wire 112.

Figure 5:
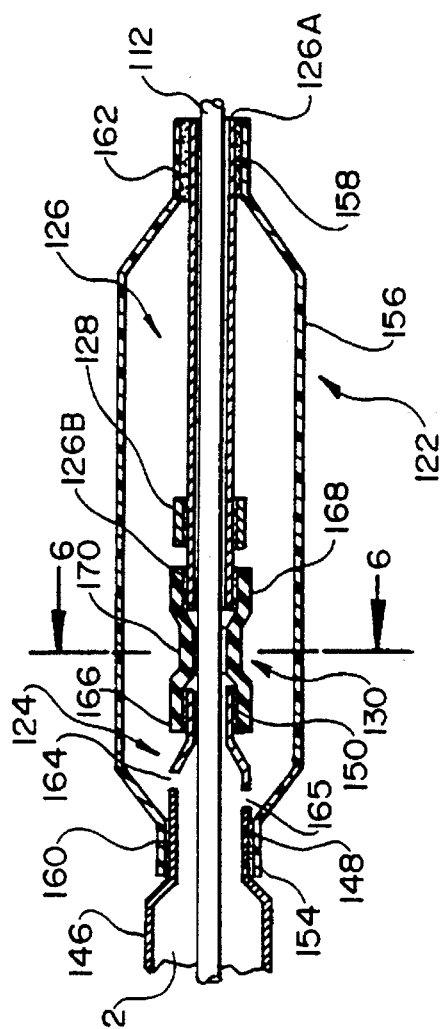
FIG. 5 is a sectional view showing in further detail the distal portion of the innerless dilatation catheter of FIG. 4.

Referring to FIGS. 4 and 5, the present invention further limits the flow of fluid in either direction between lumen 152 and the distal end of catheter 110 by the action of stretch responsive valve 130 during balloon inflation. The present invention takes advantage of a characteristic of certain balloon material: a longitudinal compliance of balloon 122. In other words, as balloon 122 is inflated, it tends to elongate. This causes the distance between proximal balloon waist 154 and distal end section 158 to increase as balloon 122 is inflated. Because proximal balloon waist 154 is secured by adhesive 160 to bond neck section 148, and distal end section 158 is attached by adhesive 162 to a distal end 126A of distal lumen extension 126, a proximal end 126B of distal lumen extension 126 tends to move away from valve neck section 150 as the balloon 122 is inflated.

As best shown in FIG. 5, stretch responsive valve 130 is preferably a stretchable tube having a proximal section 166 attached to valve neck section 150, and a distal section 168 attached to proximal end 126B of distal lumen extension 126. Intermediate section 170 of valve 130 is located in the gap between valve neck 150 and distal lumen extension 126.

Elongation of balloon 122 due to its inflation causes valve 130 to stretch. As valve 130 is stretched, the length of intermediate section 170 increases and the inner diameter of intermediate section 170 correspondingly decreases. Consequently, stretching valve 130 effectively decreases the inner diameter of a portion of the lumen extension. Preferably the amount of stretching of balloon 122, and the dimensions of valve 130 and guide wire 112, are determined while balloon 122 is inflated to pressures in its working range (approximately 0 to 18 atmospheres); the inner wall of valve 130 approximates the outer surface of guide wire 112 and substantially blocks fluid flow in either direction through valve 130.

At low inflation pressures of balloon 122, valve 130 stretches sufficiently to effect the constricting action of valve 130 and restrict fluid flow between lumen 152 and distal end 126A of distal lumen extension 126.

To achieve this valve action, proximal lumen extension 124 (formed by bond neck section 148 and valve neck section 150) and distal lumen extension 126 must be sufficiently rigid to transmit force to valve 130. In a preferred embodiment of the present invention, the amount of elongation of balloon 122 in its working range is approximately 0 to 10 millimeters.

In a preferred embodiment of the present invention, balloon 122 is a polyolefin balloon material, such as Surlyn 8527 from Dupont, which exhibits longitudinal compliance (stretching) during inflation. Proximal balloon waist 154 has an inner diameter of about 0.665 to 0.711 mm (0.0262 to 0.0280 inches) and an outer diameter of about 0.838 to 1.067 mm (0.033 to 0.042 inches) maximum depending on the inflated outer diameter of balloon 122. Distal end section 158 of balloon 122 has an inner diameter of about 0.521 to 0.584 mm (0.0205 to 0.023 inches). The overall length of balloon 122 is typically between 1 to 4 centimeters. Proximal balloon waist 154 has a length of about 8 millimeters, and distal end section 158 has a length of about 3 millimeters.

In a preferred embodiment of the present invention, distal shaft 118 and distal lumen extension 126 are formed of high density polyethylene tubing and are formed as one piece by a series of necking operations. Distal lumen extension 126 is subsequently severed from valve neck section 150 to create the gap for valve 130.

In the preferred embodiment, proximal neck section 142 has a length of about 4 millimeters, an inside diameter of about 0.533 mm (0.021 inches), and an outer diameter of about 0.635 mm (0.025 inches). Shaft section 144 has a length of about 9 centimeters, and an inner diameter of about 0.622 to 0.666 mm (0.0245 to 0.0270 inches), and an outer diameter of about 0.813 mm (0.032 inches).

Shaft section 146 has a length of about 23 centimeters, an inner diameter of about 0.508 to 0.686 mm (0.020 to 0.027 inches) and an outer diameter of about 0.635 to 0.838 mm (0.025 to 0.033 inches). Bond neck section 148 has a length of about 10 millimeters, an outer diameter of about 0.640 to 0.653 mm (0.0252 to 0.0257 inches) and an inner diameter of about 0.0508 to 0.533 mm (0.020 to 0.021 inches). Vent holes 164 and 165 are round holes about 0.178 to 0.254 mm (0.007 to 0.010 inches) in diameter. Vent hole 164 is located about 9.5 millimeters distal to shaft section 146. Vent hole 165 is located about 8.5 millimeters distal to shaft section 146. Vent hole 164 is positioned 180 degrees from vent hole 65 around the circumference of bond neck section 148, as illustrated in FIGS. 4 and 5.

Valve neck section 150 and distal lumen extension 126 have inner diameters of about 0.381 to 0.406 mm (0.015 to 0.016 inches) and outer diameters of about 0.470 to 0.508 mm (0.0185 to 0.020 inches). Valve neck section 150 has a length of about 2.5 millimeters, while distal lumen extension 126 has a length which depends on the size and length of balloon 122.

The reduced diameter sections of dilatation catheter 110, such as valve neck section 150 and distal lumen extension 126, have become oriented molecularly as a result of the necking down of the high density polyethylene tubing. This provides the additional rigidity in the axial direction necessary to transmit force from proximal balloon waist 154 and distal end section 158 of balloon 122 to valve 130.

In this preferred embodiment, valve 130 is a tube made of a polyurethane, such as Pellethane 2352-70A, or Tecothane TT-1075A from Thermedics, with an inner diameter of about 0.368 to 0.381 mm (0.0145 to 0.0150 inches) and a maximum outer diameter of about 0.508 mm (0.020 inches). Valve 130 is soaked in alcohol and then stretched over valve neck section 150 and proximal end 126B of distal lumen extension 126. In one embodiment, valve neck section 150 and proximal end 126B of distal lumen extension each include a circumferential ridge (not shown), which aids in the retention of valve 130. Proximal section 166 and distal section 168 of valve 130 are about 1.5 to 3.0 millimeters in length, while intermediate section 170 is about 1 to 5 millimeters in length in its unstretched state. The total elongation of balloon 122 is about 0 to 10 millimeters.

Marker band 128 is a band of radiopaque metal located on distal lumen extension 126 near proximal end 126B such that marker band 128 is positioned approximately in the center of balloon 1.22. Marker band 128 has an inner diameter of about 0.521 to 0.533 mm (0.0205 to 0.0210 inches) and a wall thickness of about 0.048 to 0.051 mm (0.0019 to 0.0020 inches).

Guide wire 112, used in conjunction with catheter 110, has an overall length of about 175 centimeters. The outer diameter of guide wire 112 is about 0.356 mm (0.014 inches) over the length of the body. The inner surfaces of proximal lumen extension 124, distal tureen extension 126 and valve 130 must be large enough to permit free passage of guide wire 112 when balloon 122 is not inflated, yet be in close enough proximity to guide wire 112 to allow valve 130 to create the desired seal around wire 112 while balloon 122 is in an inflated state.

Figures 6A, 6B:
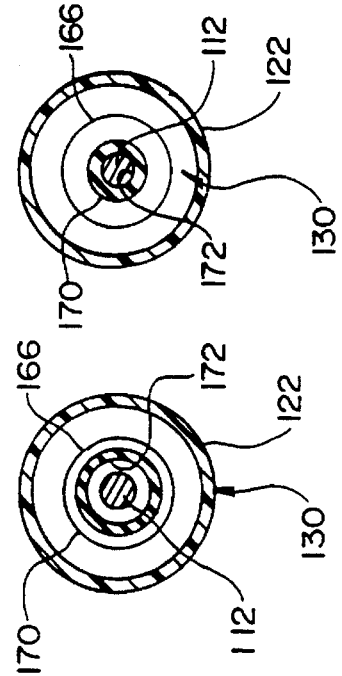
FIG. 6A is a sectional view of the innerless dilatation catheter taken on line 6—6 of FIG. 5 with an open valve.
FIG. 6B is a sectional view of the innerless dilatation catheter taken on line 6—6 of FIG. 5 with a closed valve.

As shown in FIG. 6A, in an unstretched state, the inner surface 172 of valve 130 is not in contiguous contact with guide wire 112, thereby permitting free passage of guide wire 112 through valve 130. The close proximity of guide wire 112 with inner surface 172 of valve 130 and the inner surfaces of valve neck section 150 and distal lumen extension 126 (not shown) are such that the inflation fluid distal to vent holes 164 and 165 experiences greater flow resistance with respect to the fluid flow resistance through vent holes 164 and 165 shown in FIG. 5. This yields minimal fluid leakage out the distal end of innerless dilatation catheter 110 while balloon 122 is inflating and valve 130 is constricting around guide wire 112 to block fluid flow.

FIG. 6B demonstrates valve 130 in a stretched state where the stretching decreases the inner and outer diameter of valve 130 thereby bringing inner surface 172 of valve 130 in close proximity to guide wire 112 and substantially blocking fluid flow through distal lumen extension 126 (not shown).

Other constructions of valve 130 are; also possible within the scope of the present invention. For example, the location of valve 130 within balloon 122 may be varied, and the dimensions of valve 130 can be changed. Also, valve 130 could be positioned within the distal portion of shaft 118.

Figure 7:
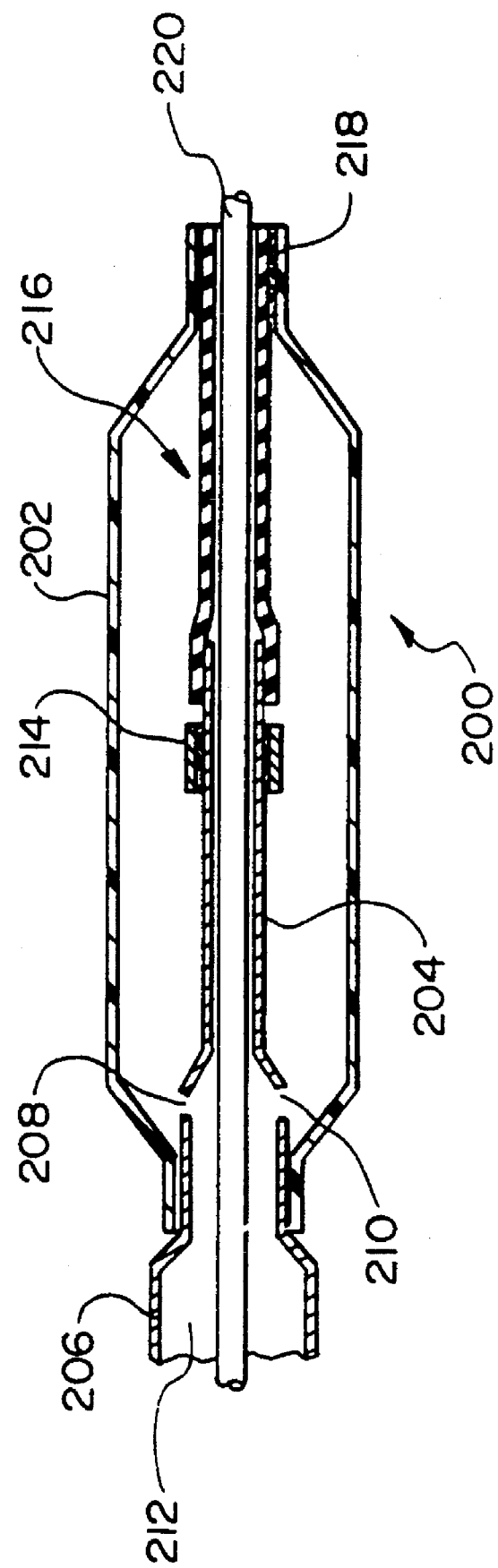
FIG. 7 is a sectional view showing another embodiment of the present invention.

A sectional view of another embodiment of the present invention is shown in FIG. 7. Distal end of catheter 200 with balloon 202 is shown with proximal lumen extension 204 connected to and extending from the distal end of shaft 206. Vent holes 208 and 210 are positioned on proximal lumen extension 204 to permit fluid communication between lumen 212 of shaft 206 and balloon 202. Unlike the embodiment shown in FIG. 5, however, the proximal lumen extension 204 extends to approximately an intermediate location within balloon 202. Marker band 214 is affixed near the distal end of proximal lumen extension 204.

The proximal end of valve 216 is connected to the distal end of proximal lumen extension 204, and the distal end of valve 216 is bonded to distal balloon waist 218. Valve 216 therefore defines the distal lumen extension 126 of FIG. 5. Like valve 130 of FIG. 5, valve 216 is axially compliant when tension is applied during balloon inflation. Other constructions of valve 216 are also possible. For example, valve 216 and distal lumen extension 204 can be incorporated into a single elastic tubular member which has compression strength in the axial direction and flexibility in tension while retaining sufficient elasticity to allow the tubular member to stretch and create a seal around guide wire 220 as balloon 202 inflates and elongates.

Guide wire 220 extends from lumen 212 of shaft 206 through proximal lumen extension 204 and valve 216 (shown in its unstretched state) and out the distal end of catheter 200. As balloon 202 is inflated and elongated, tension is applied to valve 216 thereby causing valve 216 to stretch and reduce its inner and outer diameter along essentially the entire length of valve 216. The inner diameter of a substantial length of valve 216 in a stretched state approximates the outer diameter of guide wire 220 while balloon 202 is inflated. This causes an effective obstruction of lumen 212 which essentially suppresses the flow of inflation fluid out the distal end of catheter 200 while balloon 202 is inflated.

Other constructions of innerless catheter 110 of FIG. 4 are also possible within the scope of the present invention. For example, catheter 110 can also accompany guide wires of different outer diameters (e.g., 0.254, 0.457 and 0.889 mm (0.010, 0.018, and 0.035 inches)) and balloons of different inflated diameters. The components of catheter 110 are dimensionally scaled accordingly.

Although the present invention has been described with reference to preferred embodiments, workers skilled in the art will recognize that changes may be made in form and detail without departing from the spirit and scope of the invention. For example, for different size catheters, the dimensions of the various components will vary. In the case of the proximal outer tube section 140, outer diameters preferably range from about 0.762 mm (0.0300 inches) to about 1.32 mm (0.0520 inches) maximum. Lengths range from about 81.3 to 118.8 cm (32 to 46 inches). Wall thicknesses at points of maximum thickness are about 0.064 to about 0.102 mm (0.0025 to about 0.0040 inches). The braid strands are in the range of about 0.008 mm (0.0003 inches) to about 0.038 mm (0.0015 inches) in thickness and in the range of about 0.038 to about 0.178 mm (0.0015 to about 0.007 inches) width. The weave is preferably in the range of 17.7 to 35.4 picks per cm (45 to 90 picks per inch).

In a further preferred embodiment of the invention, the flexibility of the braided proximal portion is variable, becoming progressively less stiff as one moves from the proximal to the distal end thereof. There are several ways to achieve increased flexibility along the catheter shaft. These methods include grinding, etching, secondary polymer coating and braid pick variation. Of these, pick count variation is much preferred because it does not require additional process steps and provides a much greater variation in flexibility over the length of the shaft. Specifically, it has been found that as pick count increases the stiffness decreases. Suitably the stiffness of the proximal outer tube section is in the range of 110–130 gm/cm, typically 117–130 gm/cm, at the proximal end thereof and is in the range of 15–41 gm/cm, typically 21–41 gm/cm, at the distal end thereof using a 1.27 cm segment for measurement. For a proximal outer tube portion of 101.6–152.4 cm (32–60 inches) in length the pick count desirably will increase from a low of 11.8–17.7 picks per cm (30–45 picks per inch) at the proximal end of the proximal portion to a high of 45.3–59.1 picks per cm (115–150 picks per inch) at the distal end thereof.

The composite proximal outer tube section is suitably manufactured by casting first layers of polyimide from solution over a mandrel, weaving the stainless steel braid over the polyimide first layers and then overcoating the braid with second polymer layers cast from solution. The second polymer layers will typically also be polyimide. However, to further increase the flexibility of the proximal portion at its distal end, other more flexible polymers, such as polytetrafluoroethylene, may also be used in the second polymer layers.

Table I illustrates the effect of pick count variation on the stiffness of two proximal shaft portions of differing lengths and differing inner diameter (ID) and outer diameter (OD). Measurements were taken in English units. The polymer matrix first layers were polyimide and second layers were polytetrafluoroethylene.

TABLE I

| Distance from proximal end cm (inches) | ID mm (inches) | OD mm (inches) | Picks per cm (per inch) | Stiffness* gm/cm (lbs/in) | E MPa (psi) | Kink dia. cm (inches) |
| --- | --- | --- | --- | --- | --- | --- |
| Proximal Shaft Portion A - 132.1 cm (52 inch) length | | | | | | |
| 5.1 | .757 | .965 | 14.2 | 117.7 | 2974.8 | 3.17 |
| (2) | (.0298) | (.0380) | (36) | (.6590) | (431460) | (1.25) |
| 20.3 | .757 | .965 | 17.3 | 118.0 | 2983.1 | 3.17 |
| (8) | (.0298) | (.0380) | (44) | (.6609) | (432662) | (1.25) |
| 35.6 | .757 | .968 | 18.1 | 82.3 | 2043.6 | 2.54 |
| (14) | (.0298) | (.0381) | (46) | (.4604) | (296404) | (1.00) |
| 50.8 | .759 | .975 | 22.0 | 56.2 | 1338.3 | 1.27 |
| (20) | (.0299) | (.0384) | (56) | (.3145) | (194110) | (.50) |
| 66.0 | .759 | .978 | 22.8 | 42.8 | 1003.2 | 1.02 |
| (26) | (.0299) | (.0385) | (58) | (.2396) | (145504) | (.40) |
| 81.3 | .762 | .978 | 26.8 | 37.7 | 890.0 | 1.02 |
| (32) | (.0300) | (.0385) | (68) | (.2109) | (129085) | (.40) |
| 91.4 | .765 | .996 | 52.8 | 21.2 | 452.2 | .51 |
| (36) | (.0301) | (.0392) | (134) | (.1190) | (65587) | (.20) |
| 111.8 | .765 | .996 | 56.7 | 23.1 | 492.0 | .51 |
| (44) | (.0301) | (.0392) | (144) | (.1295) | (71355) | (.20) |
| 127 | .765 | .993 | 53.5 | 26.0 | 561.3 | .51 |
| (50) | (.0301) | (.0391) | (136) | (.1454) | (81406) | (.20) |
| Proximal Shaft Portion B - 106.7 cm (42 inch) length | | | | | | |
| 5.1 | .879 | 1.069 | 13.8 | 129.3 | 2480.4 | 3.81 |
| (2) | (.0346) | (.0421) | (35) | (.7240) | (359748) | (1.50) |

TABLE I-continued

| Distance from proximal end cm (inches) | ID mm (inches) | OD mm (inches) | Picks per cm (per inch) | Stiffness* gm/cm (lbs/in) | E MPa (psi) | Kink dia. cm (inches) |
|---|---|---|---|---|---|---|
| 21.6 | .881 | 1.077 | 15.0 | 112.9 | 2077.3 | 2.54 |
| (8.5) | (.0347) | (.0424) | (38) | (.6325) | (301281) | (1.00) |
| 38.1 | .889 | 1.080 | 19.7 | 63.4 | 1179.7 | 1.02 |
| (15) | (.0350) | (.0425) | (50) | (.3552) | (171101) | (.40) |
| 54.6 | .889 | 1.085 | 22.8 | 56.9 | 1022.6 | 1.02 |
| (21.5) | (.0350) | (.0427) | (58) | (.3187) | (148318) | (.40) |
| 71.1 | .894 | 1.097 | 25.1 | 43.7 | 736.1 | .76 |
| (28) | (.0352) | (.0432) | (64) | (.2450) | (106760) | (.30) |
| 87.6 | .897 | 1.105 | 45.7 | 37.8 | 610.6 | .51 |
| (34.5) | (.0353) | (.0435) | (116) | (.2116) | (88556) | (.20) |
| 102.9 | .897 | 1.105) | 56.7 | 40.3 | 651.4 | .51 |
| (40.5) | (.0353) | (.0435) | (144) | (.2257) | (94475) | (.20) |

*cantilevered beam (one end fixed) concentrated load at free end, measured on 1.27 cm (0.5 inch) segment centered at specified distance from proximal end.

What is claimed is:

1. A catheter for insertion into a body and having proximal and distal ends, the distal end preceding and the proximal end trailing when said catheter is inserted into the body, said catheter comprising:

a tubular shaft having an exterior surface facing the body when inserted into the body, the tubular shaft having a proximal tube section and a distal tube section, the proximal tube section further having proximal and distal ends, the proximal tube section comprising a polymer encased tubular braid of stainless steel, the polymer encasement for the braid comprising at least one layer of polyimide, the braid having a weave which increases in pick count from the proximal end to the distal end of the proximal tube section such that the stiffness of the proximal tube section decreases from the proximal end to the distal end thereof.

2. A dilatation catheter as in claim 1 wherein the proximal tube section has a length of 101.6–152.4 cm (32–60 inches), a pick count at the proximal end thereof of 11.8–17.7 picks per cm (30–45 picks per inch) and a pick count at the distal end thereof of 45.3–59.1 picks per cm (115–150 picks per inch).

3. A dilatation catheter for insertion into a body and having proximal and distal ends, the distal end preceding and the proximal end trailing when said catheter is inserted into the body, said catheter comprising:

a tubular shaft having an exterior surface facing the body when inserted into the body, the tubular shaft having a proximal tube section and a distal tube section, the proximal tube section having proximal and distal ends, the proximal tube section comprising a polymer encased tubular braid of stainless steel, the polymer encasement for the braid comprising a layer of polyimide under the tubular stainless steel braid and a second polymer layer of a more flexible polymer overcoating the braid, the braid having a weave which increases in pick count from the proximal end to the distal end of the proximal tube section.

4. A catheter for insertion into a body and having proximal and distal ends, the distal end preceding and the proximal end trailing when said catheter is inserted into the body, said catheter comprising:

a tubular shaft having an exterior surface facing the body when inserted into the body, the tubular shaft having a distal tube section and a proximal braid reinforced tube section having proximal and distal ends, the proximal braid reinforced tube section comprising a polymer encased tubular braid of stainless steel, the braid having a weave which increases in pick count from the proximal braid end to the distal braid end thereof such that the stiffness of the proximal tube section decreases from the proximal end to the distal end thereof.

5. A dilatation catheter as in claim 4 wherein the proximal braid reinforced tube section has a length of 101.6–152.4 cm (32–60 inches), a pick count at the proximal braid end thereof of 11.8–17.7 picks per cm (30–45 picks per inch) and a pick count at the distal braid end thereof of 45.3–59.1 picks per cm (115–150 picks per inch).

6. A dilatation catheter as in claim 4 wherein the polymer material encasing the stainless steel braid is polyimide.

* * * * *

UNITED STATES PATENT AND TRADEMARK OFFICE
CERTIFICATE OF CORRECTION

PATENT NO. : 5,533,987
DATED : July 9, 1996
INVENTOR(S) : JAMES R. PRAY et al.

It is certified that error appears in the above-indentified patent and that said Letters Patent is hereby corrected as shown below:

Col. 8, line 11, delete "1.22" and insert -- 122 --
Col. 8, line 19, delete "tureen" and insert -- lumen --

Signed and Sealed this

First Day of October, 1996

Attest:

BRUCE LEHMAN

*Attesting Officer*   *Commissioner of Patents and Trademarks*